United States Patent [19]

Kametani et al.

[11] 4,044,076
[45] Aug. 23, 1977

[54] METHOD FOR PRODUCING PHOSPHORUS-CONTAINING POLYMERS

[75] Inventors: Yoshiya Kametani; Tetsuro Nakahama, both of Yokohama; Atsushi Kawai, Hiroshima; Koji Mimura, Otake, all of Japan

[73] Assignees: Nitto Chemical Industry Co., Ltd.; Mitsubishi Rayon Co., Ltd., both of Tokyo, Japan

[21] Appl. No.: 661,861

[22] Filed: Feb. 27, 1976

[30] Foreign Application Priority Data

Apr. 18, 1975 Japan ................................. 50-46549
Apr. 18, 1975 Japan ................................. 50-47925

[51] Int. Cl.² ............................................. C07F 9/40
[52] U.S. Cl. .............................. 260/969; 260/927 R; 260/931; 428/276; 428/277
[58] Field of Search ...................... 260/931, 969, 2 P

[56] References Cited

U.S. PATENT DOCUMENTS

| 3,014,944 | 12/1961 | Birum | 260/931 X |
| 3,371,131 | 2/1968 | Carson | 260/931 |
| 3,701,816 | 10/1972 | Nogami et al. | 260/969 X |

Primary Examiner—Richard L. Raymond
Attorney, Agent, or Firm—Oblon, Fisher, Spivak, McClelland & Maier

[57] ABSTRACT

A phosphorus-containing polymer having the formula:

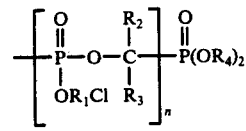

is produced by reacting a cyclic chlorophosphite compound having the formula

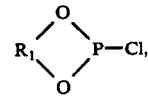

a ketone compound having the formula

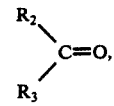

and a triorganophoshite compound having the formula $P(OR_4)_3$ in the presence of an active halide having the formula $R_5$-X wherein $R_1$ is ethylene or propylene, $R_2$ and $R_3$ are methyl or ethyl and may be the same or different, $R_4$ is an alkyl group having 1 to 4 carbon atoms or an aralkyl group in which the alkyl substituent has 1 to 4 carbon atoms and the hydrogen atoms in said alkyl and aralkyl groups may be substituted with chlorine or bromine, $R_5$ is an unsaturated or saturated aliphatic, alicyclic or aromatic group having 1 to 10 carbon atoms or combinations thereof and $R_5$ may contain a carbonyl group, sulfonyl group or nitrogen, X is a halogen, and $n$ is an integer of from 1 to 1000.

8 Claims, 2 Drawing Figures

METHOD FOR PRODUCING PHOSPHORUS-CONTAINING POLYMERS

BACKGROUND OF THE INVENTION

1. Field of the Invention

The present invention relates to a method for producing phosphorus-containing polymers, and more particularly, the present invention relates to a method for producing phosphorus-containing polymers possessing excellent acid resistance and alkali hydrolysis resistance.

2. Description of the Prior Art

It is known that phosphorus-, nitrogen-, and halogen-containing compounds are generally effective in imparting flameproofness to cellulose fibers. However, since these flameproofing chemicals are usually added to the fibers by impregnation in the step of after-treatment of the fibers, the hand feel quality and mechanical characteristics of the fibers are significantly damaged. Moreover, it is difficult by the conventional procedure to obtain fibers which maintain their flameproof characteristics after repeated washings.

Recently, in an attempt to improve this detrimental characteristic, several methods have been proposed for producing flameproof fibers which exhibit improved washing fastness by incorporating a flameproofing agent into a viscose and then wet spinning the viscose to disperse the flameproofing agent in the fibers. The flameproofing agents which are typically mixed with viscose, include various known phosphate compounds, phosphonitrile compounds, and the like. However, when the phosphate compounds are used, the fibers exhibit poor resistance to laundering, coloration of the fibers, and hydrolysis of the phosphate compounds with alkali present in the viscose.

The phosphonitrile compounds characteristically impart good flameproofness to the fibers, but they are very expensive. Furthermore, the fibers also possess poor resistance to laundering and do not retain much of the flameproofing agent. Also, the flameproofing agent oozes out of the fibers.

Recently, methods which use phosphorus-containing compounds have been proposed to solve these problems. For example, U.S. Pat. No. 3,371,131 shows that a phosphonate polymer obtained by the reaction of a ketone and cyclic chlorophosphite compound is effective as a flameproofing agent.

In fact, there are a number of methods which involve the production of similar phosphonate polymers followed by mixing the polymers with viscose and then spinning the viscose into a coagulation bath. These methods are disclosed in Japanese Pat. Publication No. 2693/73 and Japanese Pat. Laid-open Nos. 23612/72, 42125/73, 44519/73, 75816/73, 91312/73, 99417/73, 102200/73, 25218/74 and 35613/74. According to these methods, the deficiencies of the known flameproofing methods are improved, but these phosphonate polymers have the detrimental characteristic that they are partially hydrolyzed by alkali in the viscose.

A need, therefore, continues to exist for a method of improving the various mechanical and physical properties of fibers containing flameproofing agents.

SUMMARY OF THE INVENTION

Accordingly, one object of the present invention is to provide viscose fibers simultaneously possessing excellent fireproofing characteristics, excellent washing resistance and excellent retention of the flameproofing polymer in the fibers.

Another object of the present invention is to provide a method for fireproofing viscose fibers with an organo-phosphorus polymer such that the resulting fibers have substantially improved washing resistance.

Briefly, these objects and other objects of the present invention as hereinafter will become more readily apparent, can be attained by a method for preparing a phosphorus-containing polymer by reacting a cyclic chlorophosphite compound having the formula

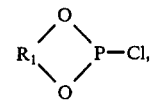

a ketone compound having the formula

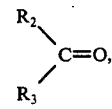

and a triorganophosphite compound having the formula $P(OR_4)_3$ in the presence of an active halide having the formula $R_5-X$ wherein $R_1$ is ethylene or propylene, $R_2$ and $R_3$ are methyl or ethyl and may be the same or different, $R_4$ is an alkyl group having 1 to 4 carbon atoms or an aralkyl group in which the alkyl substituent has 1 to 4 carbon atoms and the hydrogen atoms in said alkyl and aralkyl groups may be substituted with chlorine or bromine, $R_5$ is an unsaturated or saturated aliphatic, alicylic or aromatic group having 1 to 10 carbon atoms or combinations thereof and $R_5$ may contain a carbonyl group, sulfonyl group or nitrogen, X is a halogen, and $n$ is an integer of from 1 to 1000.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings wherein.

DETAILED DESCRIPTION OF THE PREFERRED EMBODIMENTS

Figure 1:
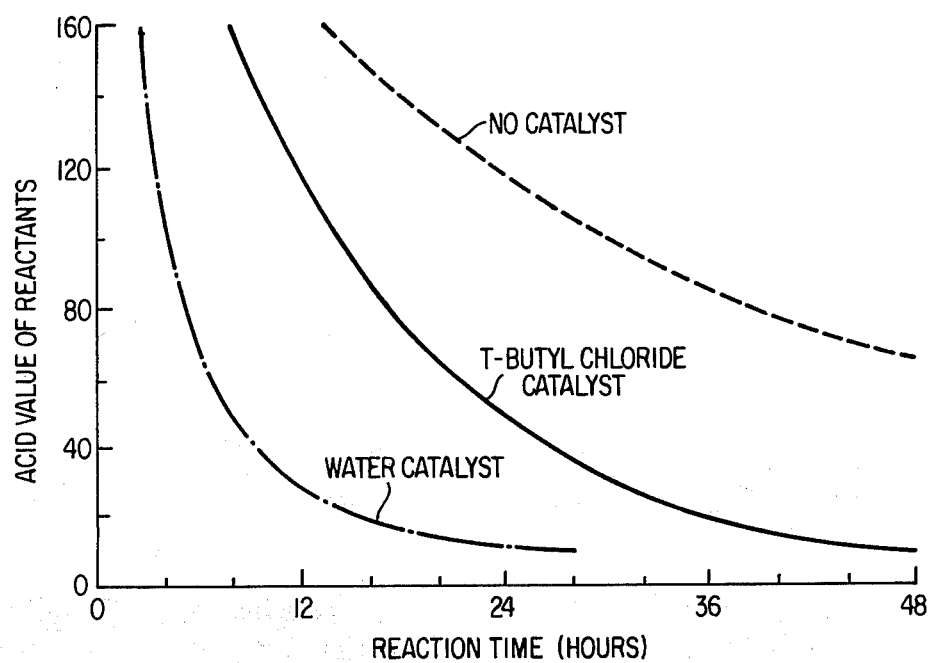
FIG. 1 is a graph which shows the relationship between reaction time and the acid value of reactants (reaction products) in the preparation of the phosphonate polymer without the presence of a catalyst, with the use of water as a catalyst and with the use of tert-butylchloride as a catalyst.

Since decreases in the retention of flameproofing agents in fibers seem to be caused by hydrolysis of the phosphonate polymers in viscose, precise experiments have repeatedly been conducted for the preparation of phosphonate polymers from the three starting materials which are a cyclic chlorophosphite compound, a ketone compound, and a triorganophosphite compound. The resultant polymer has been subjected to detailed examination with regard to structure, molecular weight distribution, and alkali hydrolysis resistance of the resultant phosphonate polymers. As a result, it has been found that when the polymers are produced using an active halide as the catalyst, phosphonate polymers are obtained which have excellent alkali hydrolysis resistance and acid resistance. It has also been found that the phosphonate polymers when incorporated into viscose and the viscose is spun, possess greatly improved retention properties in the fibers. In addition, the fibers obtained possess excellent washing resistance.

The present invention involves a method for producing phosphonate polymers by reacting a cyclic chlorophosphite compound, a ketone compound, and a trioganophosphite compound in the presence of a specific active halide.

The phosphonate polymers of the present invention are represented by the following formula:

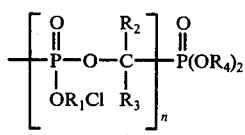

wherein $R_1$ is ethylene or propylene, $R_2$ and $R_3$ are each methyl or ethyl and may be the same or different, $R_4$ is an alkyl group of 1 to 4 carbon atoms, or an aralkyl group substituted by alkyl of 1 to 4 carbon atoms wherein the hydrogen atoms in these groups may be substituted with chlorine or bromine, and $n$ is an integer of 1 to 1000.

The cyclic chlorophosphite compounds used in the preparation of the phosphonate polymers are represented by the formula:

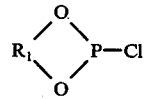

wherein $R_1$ is as previously defined. Suitable cyclic chlorophosphite compounds include ethylene chlorophosphite and propylene chlorophosphite.

The ketone compound used in the present invention is represented by the formula:

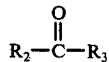

wherein $R_2$ and $R_3$ are as previously defined. Suitable examples of ketone compounds include acetone, methyl ethyl ketone and diethyl ketone.

The triorganophosphite compounds used in the present invention are represented by the formula:

wherein $R_4$ is as previously defined. Suitable triorganophosphite compounds include trimethyl phosphite, triethyl phosphite, tripropyl phosphite, tributyl phosphite, dimethylethyl phosphite, triisopropyl phosphite, tris-2-chloroethyl phosphite, tris-2-bromoethyl phosphite, tris-2,3-dichloropropyl phosphite, tris-2,3-chlorobromopropyl phosphite, tribenzyl phosphite, ethylene methyl phosphite, ethylene 2-chloroethyl phosphite, propylene 2-chloroethyl phosphite, and propylene chloropropyl phosphite.

The catalyst used in the present invention is selected from the group of active halogenated hydrocarbons, sulfonyl halides, acid halides and N-halides, and is represented by the formula:

wherein $R_5$ is as previously defined and X is a halogen such as chlorine, bromine or iodine. Suitable examples of the active halides include methyl iodide, isopropyl bromide, n-butyl chloride, iso-butyl chloride, tert-butyl chloride, allyl chloride, methallyl chloride, cyclohexyl chloride, benzyl chloride, dibenzyl chloride, phenethyl chloride, chloromethyl styrene, acetyl chloride, benzoyl chloride, cinnamoyl chloride, phthaloyl chloride, benzenesulfonyl chloride, p-toluenesulfonyl chloride, cyanuric chloride, N-chlorosuccinimide, N-bromosuccinimide, 1,3-dichlorohydantoin, 1,3-dichloro-5,5'-dmethylhydrantoin, and trichloroisocyanuric acid.

In the preparation of the polymer of the present invention it is important to react a purified cyclic chlorophosphite compound, a purified ketone compound, and a triorganophosphite compound in the presence of the active halide catalyst. The effects of the active halide catalyst can be further increased by using sufficiently purified chlorophosphite and ketone compounds, thereby resulting in phosphonate polymers possessing excellent acid and alkali resistance. Furthermore, the polymerization degree of the phosphonate polymers produced can be optionally varied by controlling the relative amount of the triorganophosphite compound reacted with the cyclic chlorophosphite.

The cyclic chlorophosphite used in the present process can be produced in very high yields by such conventional methods as reacting the corresponding glycol and phosphorus trichloride under suitable conditions. For example, 707.6 g of phosphorus trichloride and 593.8 g of 1,2-dichloroethane were charged into a 2 liter flask and then 380.5 g of propylene glycol were added to the mixture in the flask over a period of about 3 hours at 5° to 10° C. The reaction product was then purged with nitrogen gas at 5° to 10° C for about 1.5 hours to remove hydrogen chloride. Thereafter the product was distilled using a fractionating column under a reduced pressure to obtain the chlorophosphite. The purity of the chlorophosphite obtained by this method is about 99% or greater.

The ketone compound is generally purified to such an extent that the water content of the ketone is less than 0.25%. The best results are obtained when the water content of the solvent is less than 0.02%.

The following description of preferred methods of synthesizing the phosphonate polymers of the present invention.

In one method the cyclic chlorophosphite, the ketone, the triorganophosphite, and the active halide can be mixed all together. However, since the reaction is slightly exothermic, the cyclic chlorophosphite or a mixture of the cyclic chlorophosphite and the triorganophosphite is preferably gradually added to the other compounds to control heat of the reaction and to prevent side reactions. In this technique a solvent is preferably used to make the operation easier as well as to control the heat of reaction and to prevent side reactions.

In the selection of the appropriate solvent, consideration should be given to the fact that the solvent should not arrest the reaction and that it should dissolve both the reacting compounds and the reaction product. Furthermore, the product must be easily isolated from the solvent. Suitable solvents which can be effectively used in the reaction include, for example, methylene chloride, 1,2-dichloroethane, trichlene, 1,1,2,2-tetrachloroethylene, methyl choloroform, carbon tetrachloride, 1,1,2-trichloroethane, acetonitrile, tetrahydrofuran, dioxane, chloroform, benzene, toluene, xylene, monochlorbenzene, o-dichlorobenzene, and the like.

The reaction temperature is usually −50° C to 200° C, preferably 0° C to 100° C.

The progress of the reaction can be easily followed by checking the acid value of the reactants. When a polymer of high molecular weight is to be produced, the reaction is preferably monitored by checking the viscosity of the solution.

The reaction can be conducted under normal pressure or in a closed state. Preferably the reaction is conducted under a nitrogen atmosphere.

The proportions of the reacting compounds used in the reaction are as follows. The mole ratio of the cyclic chlorophosphite compound to the ketone compound is generally 1:1 to 1:1.2. The triorganophosphite which is important for determining the polymerization degree is usually employed in an amount ranging from 0.001 to 0.05 mole per mole of the cyclic chlorophosphite.

The active halide catalyst is usually employed in an amount ranging from 0.001 to 0.05 mole (0.1 to 5 mole %) per mole of the cyclic chlorophosphite compound. Even amounts of less than 1 mole % can exhibit sufficient effects.

When the polymerization reaction is conducted by using the commerically available reagents or industrial chemicals as they are obtained without further purification, the presence of small amounts of water in the reagents acts as a catalyst for the reaction so that it proceeds quite sufficiently. However, during the course of the experimental procedures for developing the reaction, it was found that when a purified cyclic chlorphosphite (the chlorophosphite is deemed pure when the I.R. spectrum of the compound exhibits no P—H bond absorption at 2430 cm$^{-1}$), a purified ketone compound, and a purified triorganophosphite compound are allowed to react in a purified inactive solvent, the progress of the polymerization reaction is very much delayed. Since the above reaction can be catalyzed by materials other than water, intensive research has been conducted on the catalytic effect exhibited by water, Lewis acid, active halides, and the like in such systems. It has been found, as a result of this research that when an active halide is used as the catalyst, phosphonate polymers are obtained which exhibit especially excellent alkali hydrolysis resistance properties.

It has been known as disclosed in, for example, U.S. Pat. No. 3,371,131, that the polymerization reaction proceeds in the presence of an acid catalyst. Furthermore, according to the precise experiments, it has been recognized that water, methanol, and ethanol also accelerate the polymerization reaction, but it has also been recognized that when Lewis acid type catalysts such as hydrogen chloride, sulfuric acid, AlCl$_3$, BF$_3$ etherate, TiCl$_4$, and the like are used, the polymerization reaction does not smoothly proceed when the reaction system is very nearly in the anhydrous state.

FIG. 1 is a graph which shows the relationship between period of reaction time and the acid value of the reactants when the phosphonate polymer is prepared at 25° C under the condition when water and tert-butylchloride are used as catalyst and when no catalyst is used. As shown in FIG. 1, the reaction is slow when no catalyst is used, and even after a lapse of 48 hours, the reactants have an acid value greater than 60. Therefore, the uncatalyzed reaction has no practical utility. When water is used as the catalyst, the reaction is rapid and after a lapse of 24 hours the acid value of the reactants decreases to about 10. However, when the resultant phosphonate polymer is mixed with viscose and the viscose is spun, the retention of the polymer in the fibers after the spinning step is about 84 to 86% and the properties of the resultant fibers are not good.

On the other hand, when tert-butylchloride is used as the catalyst, the reaction is slower than when water is used. However, as is clear from the fact that after a lapse of 48 hours the acid value of the reactants decreases to about 10, the acid value of the phosphonate polymer steadily decreases with the progress of the reaction, which is evident of the fact that tert-butylchloride is an effective catalyst for the reaction of the preparation of the phosphonate polymers. The retention of the resultant phosphonate polymer in a fibrous substrate is greater than 95% and thus the polymer can be used with satisfaction for producing flameproof fibers. It is believed that the polymerization reaction proceeds most preferably resulting in a polymer with very good properties when tert-butylchloride is used as the catalyst.

When active halides other than tert-butylchloride, which also are within the scope of the present invention, are used as the catalyst, satisfactory results can also be obtained as in the case of tert-butylchloride.

Another beneficial effect of using the active halide catalysts in the present invention is the stabilization of the resultant phosphonate polymer.

Triorganophosphite compounds are effective for the fixation of the terminal structure of the phosphonate polymer produced by the reaction of the cyclic chlorophosphite with the ketone, and they also selectively fix one terminal of the polymer. The structure of the terminal portions of the polymer has a substantial effect on the improvement of the hydrolysis resistance of the polymer. An example of a terminated polymer, wherein the terminal structure has a cyclic phosphate structure is:

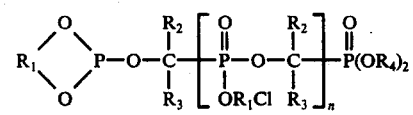

Since the phosphorus atom in the terminal cyclic phosphite group structure maintains its trivalent oxidation state, the terminal structure is unstable. Therefore, it is desirable to stablize the polymer by converting the trivalent state into the pentavalent state by heating or by some other methods.

Regarding the effect of the active halide catalyst on the polymer product, it is presumed that the terminal cyclic phosphite structure reacts with the active halide to cause a ring-opening rearrangement reaction which results in the stabilization of the terminal structure as shown below.

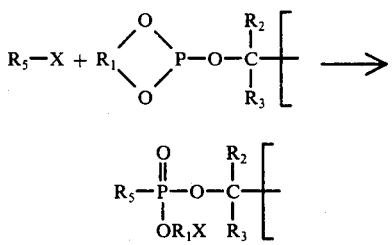

The phosphonate polymers of the present invention have excellent alkali hydrolysis resistance and are retained very well in regenerated cellulose fibers. Therefore, the phosphonate polymer of the present invention can be added to a viscose obtained by the conventional method in an amount of 5 to 40% by weight of the cellulose in the viscose and mixed homogeneously. The viscose is then spun into a coagulation bath by the conventional method. For example, a viscose having a cellulose concentration of 4 to 10% by weight, an alkali concentration of 3 to 8% by weight, a salt point of 5 to 20, and a viscosity of 40 to 500 poises (at 20° C) is preferably used. The coagulation bath preferably contains 0 to 150 g/l zinc sulfate, 10 to 120 g/l sulfuric acid, and 20 to 350 g/l sodium sulfate and is kept at a temperature of 10° to 70° C.

The addition of the phosphonate polymer to the viscose may be effected by any method which results in homogeneous mixing, but preferably the polymer is added as a solution in a suitable solvent or as an aqueous emulsion or suspension. At this time, some other phosphorus compund or flameproofing agent can be added to the viscose together with the phosphonate polymer.

The phosphonate polymers produced by the present invention can also be incorporated into various other combustible materials to provide an endurable flameproofing effect.

Having generally described this invention, a further understanding can be obtained by reference to certain specific examples which are provided herein for purposes of illustration only and are not intended to be limiting unless otherwise specified. In these examples, the terms "parts" and "percentages" are given by weight, and the water content of the sufficiently dried nitrogen gas is less than 0.01 mg/l.

EXAMPLE 1

A 1 liter separatory flask provided with a stirrer, a thermometer, a reflux condenser, a dropping funnel, and a nitrogen gas inlet device was prepared for the reaction. Into the flask were charged 380 parts of purified toluene as the reaction solvent and 253 parts of purified ethylene chlorophosphite. Then, 116 parts of purified acetone, 11 parts of purified tris-2-chloroethyl phosphite, and 1.6 parts of purified acetyl chloride were charged into a dropping funnel. The reaction mixture was cooled in an ice water bath under a flow of dry nitrogen gas and a mixture of acetone, tris-2-chloroethyl phosphite, and acetyl chloride was gradually dropped into the flask over a period of about 1.5 hours with stirring. The reaction temperature was kept at 5° to 10° C while the acetone solution was added. After completion of the addition of the acetone solution, the reactants were allowed to stand for about 48 hours at room temperature and then they were heated at 85° C for 13 hours. Thereafter, the solvent and unreacted materials were removed by distillation under reduced pressure whereby a colorless phosphonate polymer was obtained.

EXAMPLE 2

The flask used in Example 1 was employed in this example. Into the flask were charged 253 parts of purified ethylene chlorophosphite, 386 parts of purified methyl chloroform as the reaction solvent, and 15.5 parts of purified tris-2-chloropropyl phosphite. Thereafter, 116 parts of purified acetone and 1.9 parts of tert-butylchloride were charged into a dropping funnel. The reaction mixture was cooled in an ice water bath under a flow of dry nitrogen gas and mixture of acetone and tert-butylchloride was dropped from the dropping funnel with stirring. The temperature in the flask was kept at a temperature of 5° to 10° C. After completion of the addition of the acetone solution, the reactants were allowed to stand at room temperature for about 48 hours. Thereafter, the solvent and unreacted materials were removed by distillation under reduced pressure whereby a colorless glassy phosphonate polymer was obtained.

EXAMPLE 3

The same flask used in Example 1 was employed. Into the flask were charged 253 parts of purified ethylene chlorophosphite, 16.2 parts of purified tris-2-chloroethyl phosphite, and 415 parts of purified dichloromethane as the reaction solvent. Then, 144 parts of purified methylethylketone and 1.5 parts of purified allyl chloride were charged into the dropping funnel. The reaction mixutre was cooled in an ice water bath under a flow of dry nitrogen gas, and the mixture of methylethylketone and allyl chloride was dropped with stirring into the flask while the temperature in the flask was maintained at 5° to 10° C. After completion of the addition of the ketone solution, the reactants were allowed to stand at room temperature for about 48 hours and then they were heated at 40° C for 13 hours. Thereafter, the solvent and unreacted materials were removed by distillation under reduced pressure whereby a colorless glassy phosphonate polymer was obtained.

EXAMPLE 4

The same flask used in Example 1 was employed. Into the flask were charged 253 parts of purified ethylene chlorophosphite, 450 parts of purified cholorform as the reaction solvent, and 6.2 parts of purified tris-2-chloropropyl phosphite. Thereafter, 144 parts of methylethylketone and 2.5 parts of purified benzyl chloride were charged into a dropping funnel. The reaction mixture was cooled in an ice water bath under a flow of dry nitrogen gas and the mixture of methylethylketone and benzyl chloride was dropped from the dropping funnel into the flask over which time the temperature within the flask was kept at 5° to 10° C. After completion of the addition of the ketone solution, the reactants were allowed to stand at room temperature for about 48 hours. Thereafter, the solvent and unreacted materials were removed by distillation under reduced pressure whereby a colorless glassy phosphonate polymer was obtained.

EXAMPLE 5

The same flask used in Example 1 was employed. Into the flask were charged 281 parts of purified propylene chlorophosphite, 410 parts of purified 1,2-dichloroethane as the reaction solvent, and 11 parts of purified tris-2-chloroethyl phosphite. Then, 116 parts of purified acetone and 2.8 parts of purified benzyl chloride were charged into a dropping funnel. The reaction mixture was cooled in an ice water bath under a flow of dry nitrogen gas and the mixture of acetone and benzyl chloride was added to the flask from the dropping funnel with stirring. The temperature within the flask was kept at 5° to 10° C. After completion of the addition of the acetone solution, the reactants were allowed to stand at room temperature for about 48 hours and then they were heated at 85° C for 13 hours. Thereafter, the solvent and unreacted materials were removed by distillation under reduced pressure whereby a colorless glassy phosphonate polymer was obtained.

EXAMPLE 6

The same flask used in Example 1 was employed. The flask was charged with 281 parts of purified propylene chlorophosphite, 436 parts of purified carbon tetrachloride as the reaction solvent, and 9.3 parts of purified tris-2-chloropropylene phosphite. Then, a dropping funnel was charged with 144 parts of purified methylethylketone and 3.5 parts of purified benzenesulfonyl chloride. The reaction mixture was cooled in an ice water bath under a flow of dry nitrogen gas and the mixture of methylethylketone and benzenesulfonyl chloride was dropped from the dropping funnel into the flask with stirring. The temperature within the flask was kept at 5° to 10° C. After completion of the addition of the ketone solution, the reactants were allowed to stand at room temperature for about 48 hours and then they were heated at 75° C for 13 hours. Thereafter, the solvent and unreacted materials were removed by distillation under reduced pressure whereby a colorless glassy phosphonate polymer was obtained.

EXAMPLE 7

The same flask used in Example 1 was employed. The flask was charged with 281 parts of purified propylene chlorophosphite, 424 parts of purified monochlorobenzene as the reaction solvent, and 24.8 parts of purified tris-2-chloropropyl phosphite. Then, a dropping funnel was charged with 116 parts of purified acetone and 3.6 parts of purified N-bromosuccinimide. The reaction mixture was cooled in an ice water bath under a flow of dry nitrogen gas, and the mixture of acetone and N-bromosuccinimide was dropped from the dropping funnel into the flask with stirring over which time the temperature within the flask was kept at 5° to 10° C. After completion of the addition of the acetone solution, the reactants were allowed to stand at room temperature for about 48 hours and then they were heated at 85° C for 13 hours. Thereafter, the solvent and unreacted materials were removed by distillation under reduced pressure whereby a colorless glassy phosphonate polymer was obtained.

EXAMPLE 8

The same flask used in Example 1 was employed. The flask was charged with 281 parts of purified propylene chlorophosphite, 433 parts of purified acetonitrile as the reaction solvent, and 6.2 parts of purified tris-2-chloropropyl phosphite. Then, a dropping funnel was charged with 144 parts of purified methylethylketone and 4.7 parts of purified trichloroisocyanuric acid. The reaction mixture was cooled in an ice water bath under a flow of dry nitrogen gas and a mixture of methylethylketone and trichloroisocyanuric acid was dropped from the dropping funnel into the flask with stirring over which time the temperature within the flask was kept at 5° to 10° C. After the addition of the ketone solution was completed, the reactants were allowed to stand at room temperature for about 48 hours and then they were heated at 80° C for 13 hours. Thereafter, the solvent and unreacted materials were removed by distillation under reduced pressure whereby a colorless glassy phosphonate polymer was obtained.

EXAMPLE 9

A viscose, which was prepared by adding carbon disulfide in an amount of 48% of cellulose and which had a cellulose concentration of 7.5% and an alkali concentration of 4.2%, was ripened so that the viscose had a viscosity of 200 poises and a salt point of 16. To the resultant viscose was added 3.5 parts of 50% 1,2-dichloroethane solution of each of the phosphonate polymers prepared in Examples 1 to 8 and the blend was mixed to make a homogeneous viscose solution. Then, each of the viscose solutions were spun into a coagulation bath containing 18 g/l sulfuric acid, 70 g/l of sodium sulfate, and 0.4 g/l of zinc sulfate to form filaments.

The filaments withdrawn from the coagulation bath were stretched by 100% in a second bath containing 2 g/l of sulfuric acid at 80° C, and thereafter were successively treated in a third bath containing 5 g/l of sulfuric acid at 60° C to complete regeneration. The regenerated cellulose filaments were then subjected to the conventional after-treatments such as desulfurization, bleaching, acid treatment, lubricant treatment, and drying.

In the preparation of the filaments it was noticed that substantially no sticky materials were formed during the spinning operation, which was a problem when conventional phosphonate polymers were employed. Furthermore, in the present Example, the retention of the phosphonate polymers in the fibers was also substantially increased compared to the retention of the conventional phosphonate polymers. The retention of the phosphonate polymers prepared in Examples 1 to 8 are shown in Table 1.

Table 1

| Example | 1 | 2 | 3 | 4 | 5 | 6 | 7 | 8 |
|---|---|---|---|---|---|---|---|---|
| Retention % | 96.4 | 95.5 | 97.1 | 95.9 | 96.8 | 97.4 | 94.0 | 95.6 |

COMPARISON EXAMPLE 1

The same flask used in Example 1 was employed. The flask was charged with 253 parts of purified ethylene chlorophosphite, 408 parts of purified 1,2-dichloroethane as the reaction solvent, and 11 parts of purified tris-2-chlorophosphite. Then, the dropping funnel was charged with 144 parts of purified methylethylketone and 0.4 parts of water. The reaction mixture was cooled in an ice bath under a flow of dry nitrogen gas and the mixture of methylethylketone and water was dropped into the flask from the dropping funnel with stirring, during which time the temperature within the flask was kept at 5° to 10° C. After the addition of the ketone solution was completed, the reactants were allowed to stand at room temperature for about 48 hours. Thereafter, the solvent and unreacted materials were removed by distillation under reduced pressure whereby a colorless glassy phosphonate polymer was obtained. The thus obtained phosphonate polymer was added to the same viscose used in Example 9. The viscose was spun into a coagulation bath and the filaments thus formed were treated in the same manner as in Example 9 and it was found that the retention of the phosphonate polymer in the fibers was 84%.

COMPARISON EXAMPLE 2

The same flask used in Example 1 was employed. The flask was charged with 281 parts of purified propylene chlorophosphite, 410 parts of purified 1,2-dichloroethane as the reaction solvent, and 12.4 parts of purified tris-2-chloropropyl phosphite. Then, a dropping funnel was charged with 116 parts of purified acetone, and 0.9 parts of ethanol. The reaction mixture was cooled in an ice water bath under a flow of dry nitrogen gas and the mixture of acetone and ethanol was dropped from the dropping funnel into the flask with stirring over which time the temperature within the flask was kept at 5° to 10° C. After the addition of the acetone solution was completed, the reactants were allowed to stand for about 48 hours and then they were heated at 85° C for 13 hours. Thereafter, the solvent and unreacted materials were removed by distillation under reduced pressure whereby a colorless glassy phosphonate polymer was obtained. The thus obtained phosphonate polymer was treated in the same manner as in Example 9 to obtain fibers containing the polymer. The retention of the phosphonate polymer in the fibers was 85.2%, and the yield and properties of the phosphonate polymers obtained in the preceding Examples and Comparison Examples are shown in Table 2.

Table 2

| Example | Yield of phosphate polymer (part) | Molecular weight of polymer | Viscosity (poise) | Acid Value |
|---|---|---|---|---|
| 1 | 380.1 | 6900 | 3.5 | 4.1 |
| 2 | 384.9 | 6000 | 3.0 | 3.1 |
| 3 | 413.0 | 5200 | 2.5 | 2.5 |
| 4 | 404.1 | 13600 | 7.1 | 5.6 |
| 5 | 409.2 | 7500 | 3.7 | 3.8 |
| 6 | 436.0 | 11100 | 6.4 | 4.8 |
| 7 | 423.7 | 4200 | 1.8 | 2.1 |
| 8 | 434.2 | 16800 | 8.9 | 4.9 |
| Comparison Example 1 | 406 | 6300 | 4.0 | 3.8 |
| Comparison Example 2 | 408 | 6100 | 3.5 | 2.9 |

Note:
1. The measurement of molecular weight was conducted in accordance with vapor pressure equilibrium method using an HITACHI 115 Type Molecular Weight Measuring Apparatus.
2. Acid value is expressed as "mg" of KOH per gram of sample.
3. The viscosity was measured as a 50% solution by weight in dichloroethane.

The characteristics of the phosphonate polymer produced in accordance with the method of the present invention can be explained by reference to FIG. 2.

Figure 2:
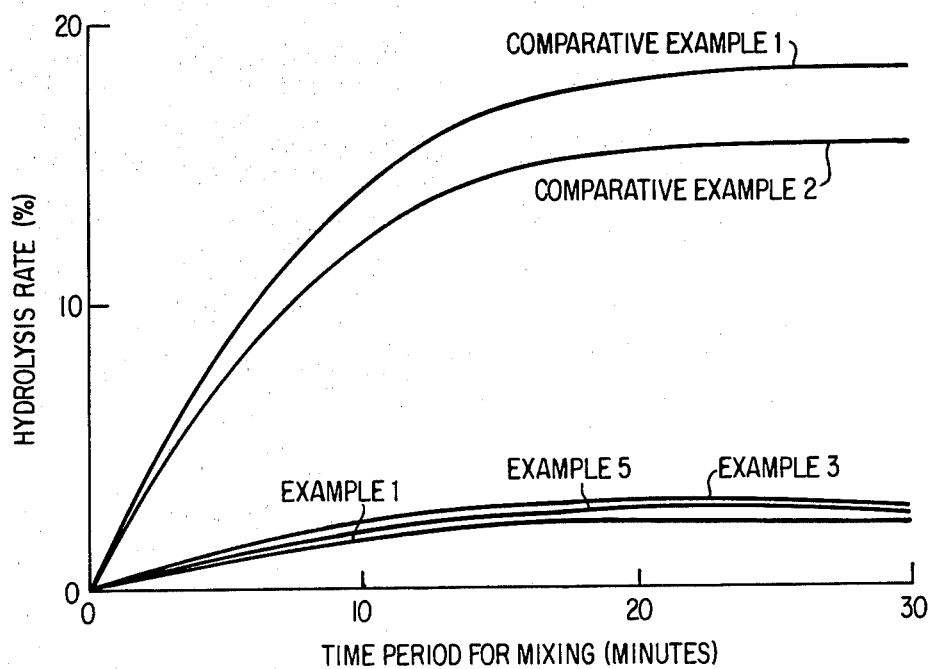
FIG. 2 is a graph which shows the relationship between the time period for mixing and the hydrolysis rate of phosphonate polymers.

FIG. 2 is a graph which shows the hydrolysis rate of the phosphonate polymers obtained in Examples 1, 3, and 5 and Comparison Examples 1 and 2 in an aqueous solution of caustic alkali. That is, FIG. 2 shows the relationship between the time of the mixing period and the hydrolysis rate of the phosphonate polymers. The hydrolysis rate was obtained by adding 40 g of a 50% solution by weight of the phosphonate polymer in 1,2-dichloroethane to 100 g of a 4% aqueous solution of caustic alkali, mixing the components with stirring in a mixer at 25° C for a fixed period of time, allowing the mixture to stand for 10 minutes, whereby it separates into two layers, sampling the aqueous layer, neutralizing it and then subjecting it to phosphorus analysis. As is clear from FIG. 2, the hydrolysis rate of the phosphonate polymers produced in accordance with the present invention in the aqueous alkali solution was substantially less than that of the phosphonate polymers obtained in Comparison Examples 1 and 2.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. In a method for producing a phosphorus-containing polymer having the formula:

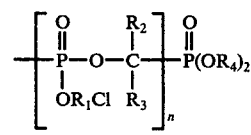

by reacting a cyclic chlorophosphite compound having the formula

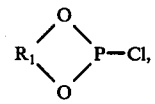

a ketone compound having the formula

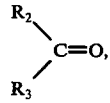

and a triorganophosphite compound having the formula $$P(OR_4)_3$$

wherein $R_1$ is ethylene or propylene, $R_2$ and $R_3$ are methyl or ethyl and may be the same or different, $R_4$ is an alkyl group having 1 to 4 carbon atoms or an aralkyl group in which the alkyl substituent has 1 to 4 carbon atoms and the hydrogen atoms in these groups may be substituted with chlorine or bromine, and $n$ is an integer of from 1 to 1000, the improvement which comprises:
reacting said compounds in the presence of an active halide represented by the formula $$R_5-X$$

wherein $R_5$ is an unsaturated or saturated aliphatic, alicyclic or aromatic group having 1 to 10 carbon atoms or a combination thereof, and $R_5$ may contain a carbonyl group or a sulfonyl group and X is halogen at a temperature of from −50° C to 200° C.

2. The method of claim 1, wherein the reaction is conducted in a solvent selected from the group consisting of toluene, chloroform, methylchloroform, dichloromethane, 1,2-dichloroethane, trichloroethylene, chlorobenzene, carbon tetrachloride, and acetonitrile.

3. The method of claim 1, wherein the reaction is conducted at a temperature of from 0° C to 100° C.

4. The method of claim 1, wherein said ketone compound is used in an amount of 1 to 1.2 mole per mole of said cyclic chlorophosphite compound.

5. The method of claim 1, wherein said triorganophosphite compound is used in an amount of 0.001 to 0.05 mole per mole of said cyclic chlorophosphite compound.

6. The method of claim 1, wherein said active halide is a compound selected from the group consisting of halosuccinimides, halohydantoin, halohydantoin compounds, cyanuric chloride and trichloroisocyanuric acid.

7. The method of claim 1, wherein said active halide is used in an amount of 0.001 to 0.05 mole per mole of said cyclic chlorophosphite compound.

8. The method of claim 1, wherein all of said cylic chlorophosphite compound, ketone compound, and triorganophosphite compound are purified in advance.

* * * * *

UNITED STATES PATENT AND TRADEMARK OFFICE
CERTIFICATE OF CORRECTION

PATENT NO. : 4,044,076
DATED : August 23, 1977
INVENTOR(S) : YOSHIYA KAMETANI ET AL It is certified that error appears in the above-identified patent and that said Letters Patent are hereby corrected as shown below:

Column 8, line 48, delete "450" and insert therefor --405--.

Column 11, in Table 2, second column heading, delete "phosphate" and insert therefor --phosphonate--.

Signed and Sealed this

Twenty-first Day of February 1978

[SEAL]

Attest:

RUTH C. MASON
Attesting Officer

LUTRELLE F. PARKER
Acting Commissioner of Patents and Trademarks